United States Patent [19]

Nakagawa et al.

[11] 4,226,539

[45] Oct. 7, 1980

[54] CYLINDRICAL BODY APPEARANCE INSPECTION APPARATUS

[75] Inventors: Yasuo Nakagawa; Hiroshi Makihira, both of Yokohama; Toshimitsu Hamada, Tokyo, all of Japan

[73] Assignee: Hitachi, Ltd., Japan

[21] Appl. No.: 863,345

[22] Filed: Dec. 22, 1977

[30] Foreign Application Priority Data

Dec. 24, 1976 [JP] Japan .................................. 51/154883
Dec. 24, 1976 [JP] Japan .................................. 51/154884
Apr. 8, 1977 [JP] Japan .................................. 52/39508

[51] Int. Cl.² ........................................ G01N 21/48
[52] U.S. Cl. ................................... 356/445; 250/563; 356/73
[58] Field of Search ............... 356/237, 73, 209, 445, 356/446; 250/223, 223 R, 223 B, 224, 562, 563; 209/538, 552, 577, 587, 598

[56] References Cited

U.S. PATENT DOCUMENTS

| 2,857,800 | 10/1958 | Stevens | 250/224 |
| 3,355,014 | 11/1967 | Howles | 250/224 |
| 3,584,963 | 6/1971 | Wisner | 250/563 X |
| 3,812,349 | 5/1974 | Gugliotta et al. | 250/223 R |
| 3,818,223 | 6/1974 | Gibson et al. | 250/223 |
| 3,980,567 | 9/1976 | Benini | 250/223 |

OTHER PUBLICATIONS

*Metrology and Inspection,* Autumn 1969, "Automatic Inspection of Fuel Element Pellets," Published by Vernon Instrument Co., Ltd.

"Citizen Fuel-Element Pellets Automatic Inspection Machine," Published by Citizen Watch Co., Ltd.

*Primary Examiner*—John K. Corbin
*Assistant Examiner*—Bruce Y. Arnold
*Attorney, Agent, or Firm*—Craig & Antonelli

[57] ABSTRACT

An automatic cylindrical body appearance inspection apparatus comprises a cylindrical body appearance detecting device including rotating means for rotating the cylindrical body around its axis at a constant speed and detecting means for optically picking up an image of a cylindrical surface of the cylindrical body rotated by the rotating means and one-dimensionally scanning the image on a plane of real image thereof in a predetermined direction to extract a base line of the cylindrical surface of the cylindrical body as an image signal, an end surface appearance detecting device including a pair of detecting means each for optically picking up an image of each of opposite end surfaces of the cylindrical body and one-dimensionally scanning the image on a plane of real image thereof in a direction transverse to the predetermined direction to extract an image signal, transporting means for transporting the cylindrical body while it is positioned, from the cylindrical surface appearance detecting means to the end surface appearance detecting means and determining means for determining pass or fail or grade of a defect pattern on the surfaces of the cylindrical body based on the image signals derived from the cylindrical surface appearance detecting device and the end surface appearance detecting device, whereby the appearance of the cylindrical surface and the end surfaces of the cylindrical body under test is automatically inspected.

17 Claims, 24 Drawing Figures

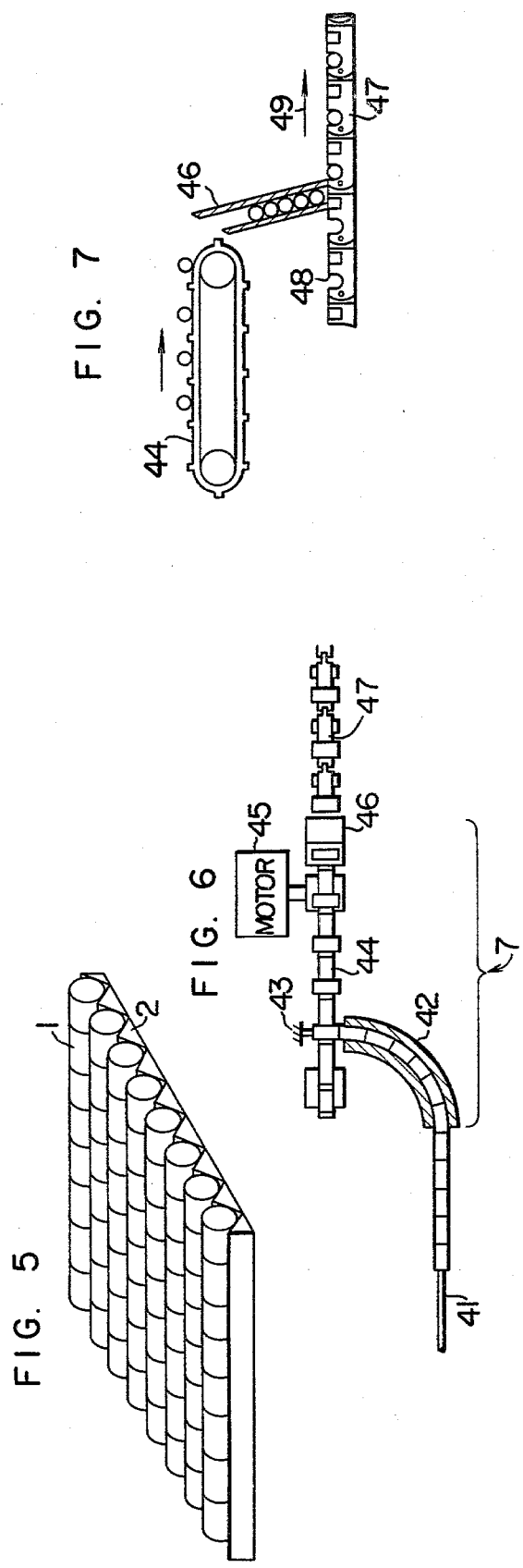

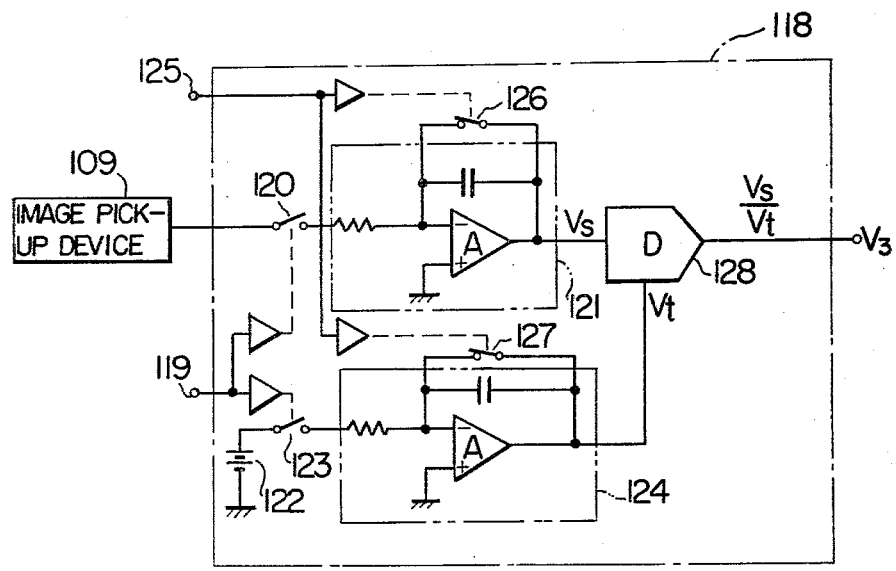
F I G. 17
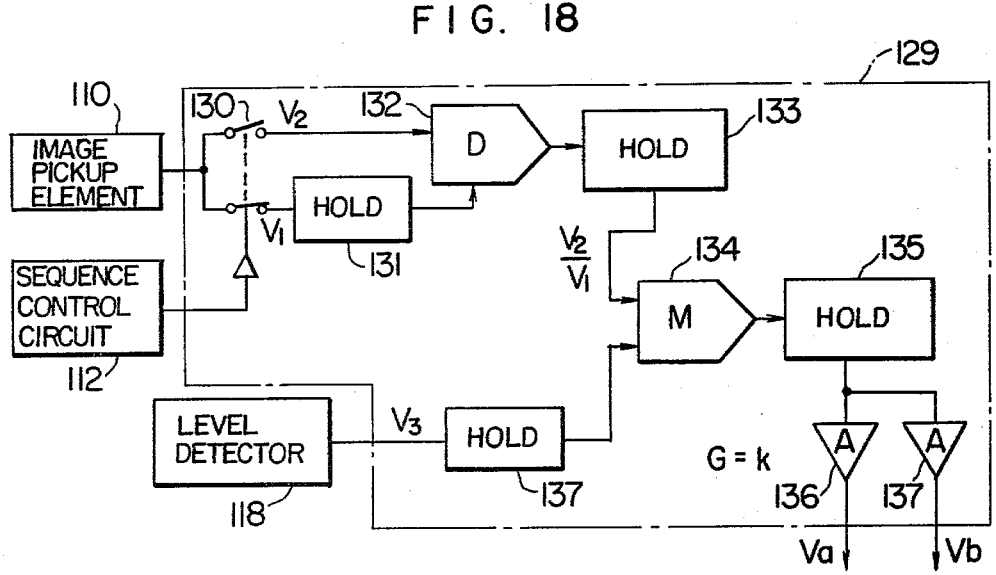
F I G. 18

CYLINDRICAL BODY APPEARANCE INSPECTION APPARATUS

LIST OF PRIOR ART REFERENCES (37 CFR 1.56 (a))

The following references are cited to show the state of the art:
1. The article "Automatic Inspection of Fuel-element Pellets" disclosed in "Metology and Inspection" Autumn 1969 published by Vernon Instrument Co., Ltd.
2. The article "Automatic Inspection of Surface Defect of Function Component" disclosed in pages 117–124 of Japanese Journal "Mechanical Automation" Vol. 5 No. 12, 1973
3. The explanatory "CITIZEN Fuel-element Pellets Automatic Inspection Machine" published by Citizen Watch Co., Ltd.

BACKGROUND OF THE INVENTION

The present invention relates to a cylindrical body appearance inspection apparatus for inspecting a flow, crack or pinhole on a surface of a cylindrical body such as mechanical part, e.g. bearing roller, or uranium pellet for use as nuclear fuel.

A prior art cylindrical body appearance inspection apparatus such as that disclosed in the article entitled "Automatic Inspection of Fuel-Element Pellets" (Metrology and Inspection, Autumn 1969) detects any chipping on a surface of a pellet by moving the pellet at a constant speed in a multi-jet air-gauging ring with the aid of push-through plunger in addition to a walking beam and senses any corner chipping of the pellet by carrying the pellet between two sensing heads which couple electro-pneumatic cells, by a walking beam transfer mechanism. However, since the prior art apparatus detects the chip of the cylindrical body by air-gauging method, it has a low resolution power and could not detect a crack of very small width. Further, because of the air-gauging method, it is difficult to detect a small chip on an edge of an end surface of the pellet or at an end of a cylindrical surface, that is, a chip close to a corner of the pellet.

SUMMARY OF THE INVENTION

It is a primary object of the present invention to provide a cylindrical body appearance inspection apparatus which optically detects any small defect such as a crack over the entire surface of a cylindrical body and opposite end surfaces of the cylindrical body to inspect the appearance of the cylindrical body with high precision and in a continuous and automatic manner.

According to the present invention, a cylindrical body appearance inspection apparatus is provided which comprises a cylindrical surface detecting device including rotating means for rotating the cylindrical body around its axis at a constant speed and detecting means for optically picking up an image of the cylindrical surface of the cylindrical body rotated by the rotating means and at least one-dimensionally scanning the image on a plane of real image thereof to detect a base line band area of a small width parallel to the axis of the cylindrical body as an image signal, end surface appearance detecting means including first transporting means for sequentially transporting a plurality of cylindrical bodies with their axes being in parallel to each other and detecting means for optically picking up an image of each of the end surfaces of the cylindrical bodies transported by the first transporting means for two-dimensionally scanning the image on a plane of real image thereof while moving the small width band area in parallel scans to extract an image signal, second transporting means for transporting the cylindrical bodies between the cylindrical surface appearance detecting means and the end surface appearance detecting means from one to the other, and determining means for determining pass or fail or grade of a defect pattern on the surfaces of the cylindrical body based on the image signals derived from the cylindrical surface appearance detecting means and the end surface appearance detecting means, whereby the appearance on the cylindrical surface and the end surfaces of the cylindrical body under test is automatically inspected.

In order to attain the above object, the present invention uses the principle of the object surface inspection apparatus disclosed in copending U.S. Patent Application Ser. No. 859,206, now U.S. Pat. No. 4,162,126, filed Dec. 9, 1977 entitled "Surface Defect Test Apparatus" also assigned to the assignee of the present invention, to discriminate a smooth surface from a flaw surface.

Further, in the present invention, in order to facilitate the inspection of the appearance of the cylindrical body, the end surface detecting means is provided in addition to the cylindrical surface detecting means, and both detecting means are coupled by the transporting means so that the cylindrical body can be efficiently subjected to test by both the detecting devices. In the cylindrical surface detecting means, the cylindrical body is held to be rotated around its axis at a constant speed and lights are directed onto the cylindrical surface from two opposite directions at an oblique angle to a base line of the cylindrical surface based on the principle of the object surface inspection apparatus of the above-identified application, and scattered light from a small width band area on the cylindrical surface along the base line thereof is detected by a detector positioned perpendicularly above the band area to produce an image signal representative of the brightness of the band area. Such an image signal is repetitively detected from successive small band areas as the cylindrical body rotates so that the entire cylindrical surface is scanned. The image signals thus derived are processed to determine the presence or absence of defects on the cylindrical surface.

On the other hand, in the end surface detecting means, a portion of the cylindrical surface of the cylindrical body is held to be moved in the direction transverse to the axis thereof, and optical object surface inspection apparatus which use the principle of the above-identified application are arranged facing the opposite end surfaces of the cylindrical body along the path of movement of the cylindrical object to detect lights reflected from small width band areas on the opposite end surfaces (which areas are spaced in the direction transverse to the direction of movement of the cylindrical body), which lights are indicative of the surface conditions. The detection is repeated at an appropriate time interval as the cylindrical body moves so that the entire surface of the opposite end surfaces are scanned. The image signals thus derived are processed to determine the presence or absence of defect on the opposite end surfaces.

The transporting means for transporting the cylindrical object between the cylindrical surface detecting means and the end surface detecting means from one to the other preferably has a function to convert the orientation of the cylindrical body taken one of one of the detecting means to the orientation for the other detecting means, because it is desirable that the cylindrical bodies are sequentially fed into the cylindrical surface detecting means in the axial direction with the cylindrical bodies being closely arranged side by side while the cylindrical bodies are sequentially fed into the end surface detecting means with the axes of the cylindrical bodies being arranged in parallel with each other.

In the cylindrical surface detecting means, a transport mechanism is simplified such that the cylindrical bodies are sequentially fed while they are closely arranged, and an effective test area for the cylindrical bodies is expanded while eliminating the boundaries of the end surfaces of the cylindrical bodies so that the appearance of the cylindrical bodies can be optically inspected over an area which extends very closely to the boundaries. The end surface appearance detecting means detects the image signal by an image pickup device which scans the cylindrical body transported by the transporting means in the predetermined direction, in the direction transverse to the predetermined direction, and discriminates the image signal by a predetermined threshold to inspect the end surfaces of the cylindrical body by a digital pattern derived from the discriminated image signal. Before picking up the image of the end surfaces of the cylindrical body by the image pickup device, the threshold described above must be adjusted in accordance with an average brightness of the end surfaces of the cylindrical body which changes from body to body or changes with aging of an illumination source. To this end, a member acting as a reference surface is arranged in the transporting means and an auxiliary image pickup device for detecting average levels $V_1$ and $V_2$ of the brightness of the reference surface of the member and the end surface of the successively transported cylindrical bodies. An average output level $V_3$ of the image signal derived by detecting the reference surface of the member by the image pickup device is also obtained. Based on the average levels $V_1$ and $V_2$ and the average output level $V_3$, the threshold V is determined by the following relation: $V = KV_2 \cdot (V_3/V_1)$, where K is a constant.

BRIEF DESCRIPTION OF THE DRAWINGS

FIG. 4 shows an overall configuration illustrating one embodiment of the cylindrical body appearance inspection apparatus of FIG. 1.

FIG. 5 shows a cylindrical body carrying tray in the embodiment of FIG. 4.

FIG. 6 is a plan view showing one embodiment of an attitude conversion mechanism for the cylindrical body in the embodiment of FIG. 4.

FIG. 7 shows a side elevational view of FIG. 6.

FIG. 17 shows a circuit diagram of an average output level detector shown in FIG. 15.

FIG. 18 shows a circuit diagram of a threshold establishing circuit shown in FIG. 15.

DESCRIPTION OF THE PREFERRED EMBODIMENTS

Figure 1:
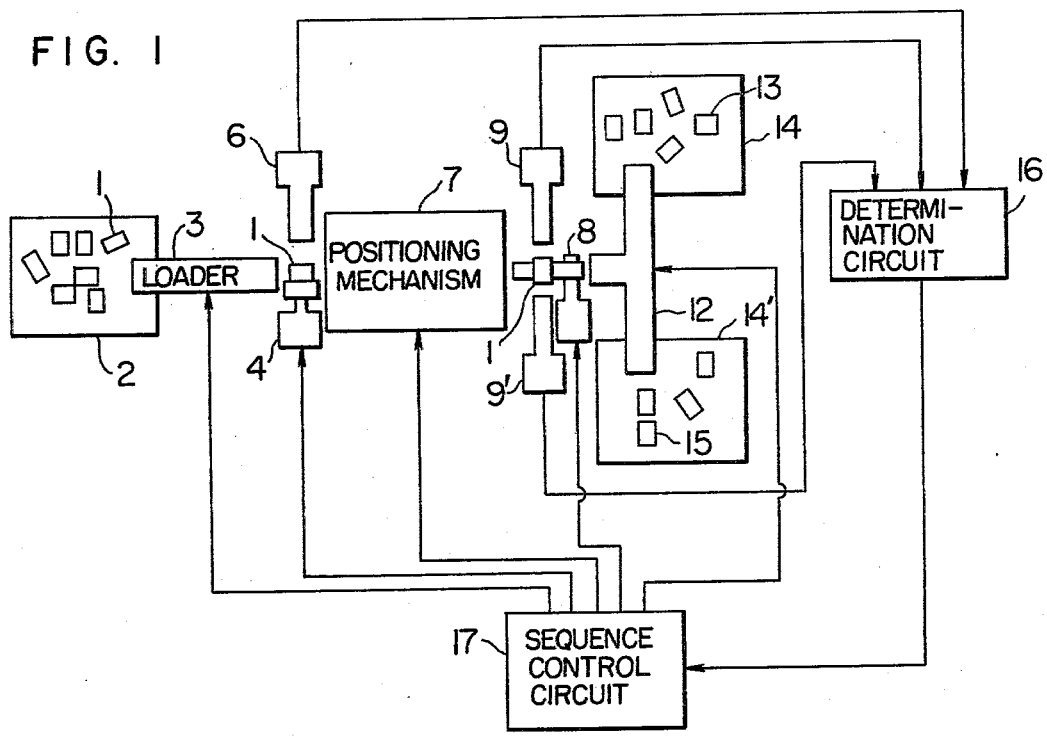
FIG. 1 is a schematic configuration showing a cylindrical body appearance inspection apparatus of the present invention.

First, it should be noted that the same reference numerals in each figure are applied to like parts.

FIG. 1 shows a schematic configuration of one embodiment of the cylindrical body appearance inspection apparatus of the present invention. The cylindrical body appearance inspection apparatus comprises a loader 3, a cylindrical body rotating mechanism 4, a cylindrical surface detecting head 6, a cylindrical body transporting, attitude converting and positioning mechanism 7, a cylindrical body horizontal movement mechanism 8, end surface detecting heads 9 and 9', an unloader 12, a determination circuit 16 and a sequence control circuit 17. The cylindrical surface detecting head 6 and the determination circuit 16 will be discussed in detail hereinafter. The end surface detecting heads 9 and 9' will also be described in detail hereinafter. A cylindrical body 1 is loaded in the cylindrical body appearance inspection apparatus while it is carried by a loading tray 2. The loader 3 picks up the cylindrical body 1 and loads it at a predetermined position in the cylindrical body rotating mechanism 4, which rotates the cylindrical body 1 around its axis. The rotating cylindrical body 1 is sensed by the detecting head 6.

Figure 2:
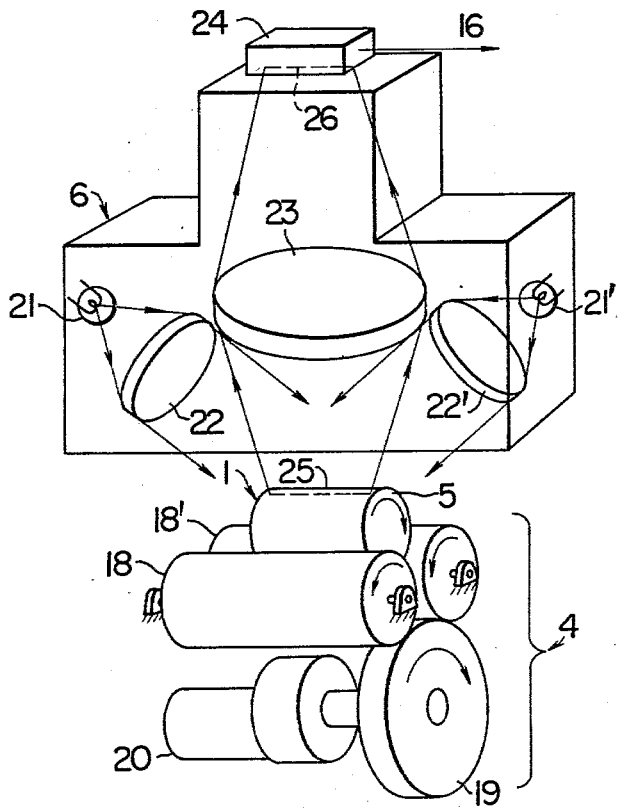
FIG. 2 is a perspective view showing a cylindrical body rotating mechanism and a detection head shown in FIG. 1.

A specific embodiment of a cylindrical surface detecting section comprising the cylindrical body rotating mechanism 4 and the cylindrical surface detecting head 6 is shown in FIG. 2. The cylindrical body 1 is mounted on a pair of rotating rollers 18 and 18', which are rotated by a motor 20 through a friction wheel 19. As a result, the cylindrical body 1 is rotated on the rollers 18 and 18'. The detecting head 6 includes illumination lamps 21 and 21' and illumination optical systems 22 and 22' by which collimated light beam are directed on the cylindrical surface 5 of the cylindrical body 1 from opposite oblique directions such that a real image of a base line 25 on the cylindrical surface 5 of the cylindrical body 1 is focused on an image pickup device 24 through a focusing lens. The image pickup device 24 may be a linear solid-state image pickup device such as photodiode array or charge coupled device (CCD). The linear image pickup device may be an array of approximately 500 or 1000 elements, each having a size of 13 μm×13 μm, arranged in a line at a pitch of approximately 25 μm. The cylindrical object 1 may have a width (length of the base line 25) of approximately 10 mm, and the focusing lens 23 may have a magnification factor of approximately unity. In this case, the 500 element array may have the length of approximately 12.5 mm, which is long enough to detect the image, and has a resolution power of approximately 25 μm. If the magnification factor of the focusing lens 23 is approximately doubled and the 1000-element array is used, the resolution power will be approximately 12.5 μm. Through the rotation of the cylindrical body 1 and the scan of the image pickup device 24, a two-dimensional image of the cylindrical surface 5 is obtained.

Figure 3:
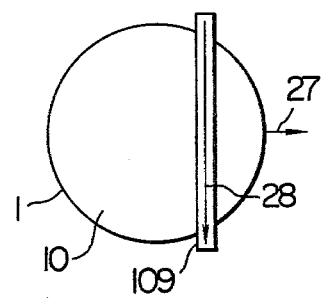
FIG. 3 is a diagram illustrating two-dimensional detection of end surfaces of the cylindrical body.

While FIG. 2 shows the linear image pickup device as the detecting device, the cylindrical surface may be scanned by a laser beam or a flying spot and a reflected light therefrom may be detected by a photomultipier or the like. The image of the cylindrical surface sensed by the detecting head 6 is evaluated by the determination circuit 16. After the detection of the cylindrical surface, the cylindrical body 1 is loaded to the cylindrical body horizontal movement mechanism 8 by the cylindrical body transporting, attitude converting and positioning mechanism 7. The cylindrical body 1 moves on the mechanism 7 from left to right, as viewed in FIG. 1. As shown in FIG. 3, through the movement 27 of the cylindrical body and the scan 28 of the image pickup device in the transverse direction, a two-dimensional image of an end surface 10 is obtained. The pair of detecting heads 9 and 9' are provided to detect the opposite end surfaces. The cylindrical body 1 may have a diameter of approximately 10 mm. In this case, the detecting head may be the one similar to the linear solid-state image pickup device shown in FIG. 2. Other two-dimensional image pickup devices, such as laser scan device, a flying spot device or TV camera may be used as the detecting head. Since the TV camera has a resolution power of approximately 1/256, when it is used to detect the object of 10 mm length, it can detect only 10/256 mm=40 μm. The image signals derived from the end surface detecting heads 9 and 9' are then evaluated by the determination circuit 16. Based on the evaluation for the cylindrical surface 5 and the end surface 10, the cylindrical body is sorted by the unloader 12 and transported to unloading trays 14 and 14'.

FIG. 4 shows a more specific embodiment of the present invention. The determination circuit and the sequence control circuit are omitted in FIG. 4. The apparatus of FIG. 4 handles the cylindrical bodies arranged on the cylindrical body tray 2 as shown in FIG. 5. The loading tray 2 is driven stepwise by a tray feed mechanism 30 and a tray drive motor 29 and the cylindrical bodies 1 on the loading tray 2 are loaded by the loading mechanism 35, row by row, on the rotating rollers 18 and 18' at the cylindrical surface detecting section loading position 37. The rows of the loaded cylindrical bodies are rotated by 120° by a station position changeover mechanism 40 and moved to the cylindrical surface detecting position 38. In this case, the mechanism 40 rotates stepwise by 120° at a time while maintaining the horizontal position of the rotating rollers 18 and 18' by a planetary gear (not shown). At the position 38, the row of the cylindrical bodies is rotated at a constant speed by the rotation of the rotating rollers 18 and 18'. Then rotating cylindrical bodies are detected by the detecting head 6, which is moved stepwise by a head drive motor 33 and a movement mechanism 34 to detect the cylindrical bodies one by one. After the cylindrical bodies have been detected, the row of the cylindrical bodies is rotated stepwise to the unloading position 39 by the station position changeover mechanism 40. The row of the cylindrical bodies on the rotating rollers 18 and 18' are fed to the cylindrical body transporting and attitude conversion mechanism 7 by the unloading mechanism 36. The row of the cylindrical bodies are rotated stepwise by 120° at a time while they are horizontally oriented by a planetary gear (not shown). Therefore, when the cylindrical surfaces thereof are to be detected, at least three pairs of the rotating rollers 18 and 18' are provided such that one pair of rotating rollers 18 and 18' are at the cylindrical surface detecting position 38 while another pair of rotating rollers 18 and 18' are loading the cylindrical bodies and the third pair of rotating rollers 18 and 18' are unloading the cylindrical bodies. In this manner, waiting times for loading and unloading can be reduced.

In the mechanism 7, the attitude of each cylindrical body is converted by 90° and the cylindrical body is loaded to the horizontal movement mechanism 8 without disturbing the order. FIG. 6 shows one embodiment of the mechanism 7. The cylindrical body at the unloading position 39 of the cylindrical surface detecting section is fed to the mechanism 7 by a pusher 41 of the unloading mechanism 36 of the cylindrical surface detecting section. In the mechanism 7, the orientation of the cylindrical bodies is converted by 90° by a guide 42 and the cylindrical bodies are fed to a conveyer 44. When the cylindrical bodies have been moved to a position defined by the stopper 43, they are carried by the conveyer 44 and fed to a shooter 46. The cylindrical bodies are temporarily stocked in the shooter 46 and then sequentially loaded to cylindrical body receiving channels 48 of an end surface detecting conveyer 47, which is moved in the direction of an arrow 49 at a constant speed.

In this manner, the attitude converted cylindrical bodies move past the detecting heads 9 and 9' at the constant speed for the detection of the end surfaces 10. In detecting the end surfaces 10, when the distances between the opposite end surfaces of the cylindrical bodies are not constant but change from body to body, the end surfaces must be positioned by end surfaces positioning mechanisms 50 and 50'.

Figure 8:
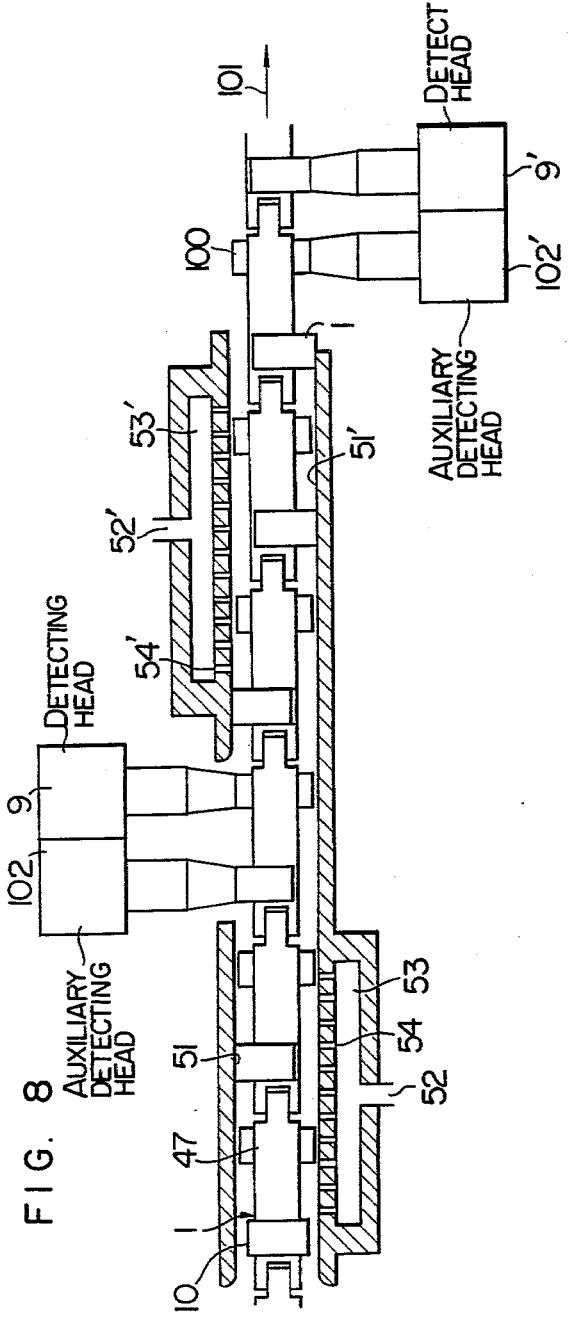
FIG. 8 is a plan view illustrating an end surface positioning method in detecting the end surface in the embodiment shown in FIG. 4.

FIG. 8 shows one embodiment of the end surface positioning mechanism. The cylindrical body 1 is in the channel 48 (FIG. 7) of the conveyer 47. In order to position the end surface 10 of the cylindrical body 1, it is abutted against a positioning plate 51. This is carried out by applying compressed air to the opposite end surface. The compressed air from an air pressure port 52, a chamber 53 and an exhaust port 54 is applied to the end surface of the cylindrical body 1 to abut the cylindrical body 1 against the positioning plate 51. After positioning the cylindrical body 1 in this manner, one end surface is detected by the detecting head 9. Then, the opposite end surface is positioned by the same mechanisms 51'–54' and detected by the head 9'.

After the detection of the cylindrical surface 5 and the end surfaces 10, the cylindrical body 1 is picked up and sorted to one of the unloading trays 14, 14' and 14" in accordance with the grade of the detection result. FIG. 4 shows an example where the cylindrical body 1 is sorted to one of three classes.

Figure 9:
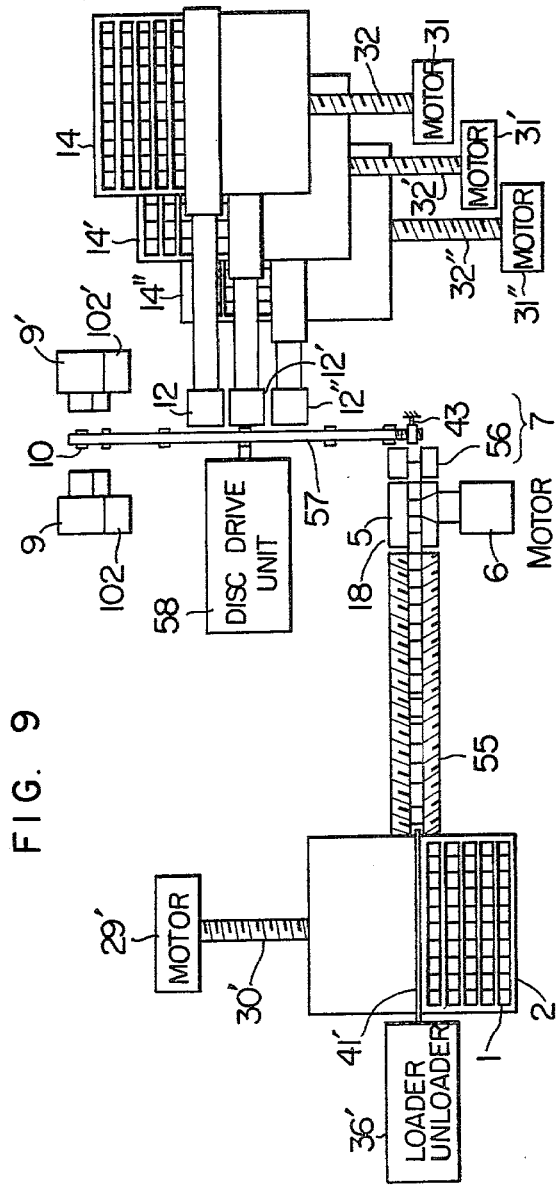
FIG. 9 shows an overall configuration of an alternative embodiment from that of FIG. 4.

FIG. 9 shows another embodiment of the present invention. Again, in FIG. 9, the determination circuit and the sequence control circuit are omitted. The embodiment of FIG. 9 comprises the loading tray 2, the loading and unloading mechanisms 36', 41', 29' and 30' and the rotating mechanism for feeding the cylindrical bodies by a load screw, which rotating mechanism includes three rotating rollers 55 having lead screws, three constantly rotating rollers 18, three dummy rollers 56 and a stopper 43, a rotating disc 57 for accommodating the cylindrical bodies 1, a rotating disc drive unit 58, the end surface detecting heads 9 and 9', the cylindrical body unloader 12, the unloading associated mechanisms 31 and 32, and the unloading tray 14.

The cylindrical bodies fed to the apparatus by the pusher 41' of the loader are pushed from left to right, as viewed in FIG. 9, by the friction force of the three rotating rollers having lead screws, and packed rightward by the rotating disc 57. Under this condition, the cylindrical bodies are rotated at a constant speed by the rotating rollers 55 and the constantly rotating role rollers 18. The cylindrical surfaces of the cylindrical bodies are then detected by the detecting head 6. The rotating disc 57 rotates in front of the stopper 43. The rotating disc 57 has an aperture of a size which allows the cylindrical body to be passed therethrough. When the aperture reaches in front of the cylindrical body, the cylindrical body, which is urged from the left, is moved into the aperture and abuts against the stopper. Thus, the cylindrical body rotates with the rotating disc 57 while it is held in the aperture of the rotating disc. In this manner, one cylindrical body is removed and the next cylindrical body is brought in front of the cylindrical surface detecting head 6. The opposite ends of the cylindrical body held in the aperture of the rotating disc 57 are detected by the end surface detecting heads 9 and 9'. In accordance with the result of the determination, the cylindrical body is sorted to a class and fed to a corresponding unloading tray.

Figure 10:
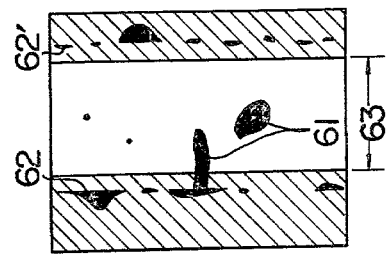
FIG. 10 shows a pattern obtained from cylindrical surfaces of closely aligned cylindrical bodies.
Figure 11:
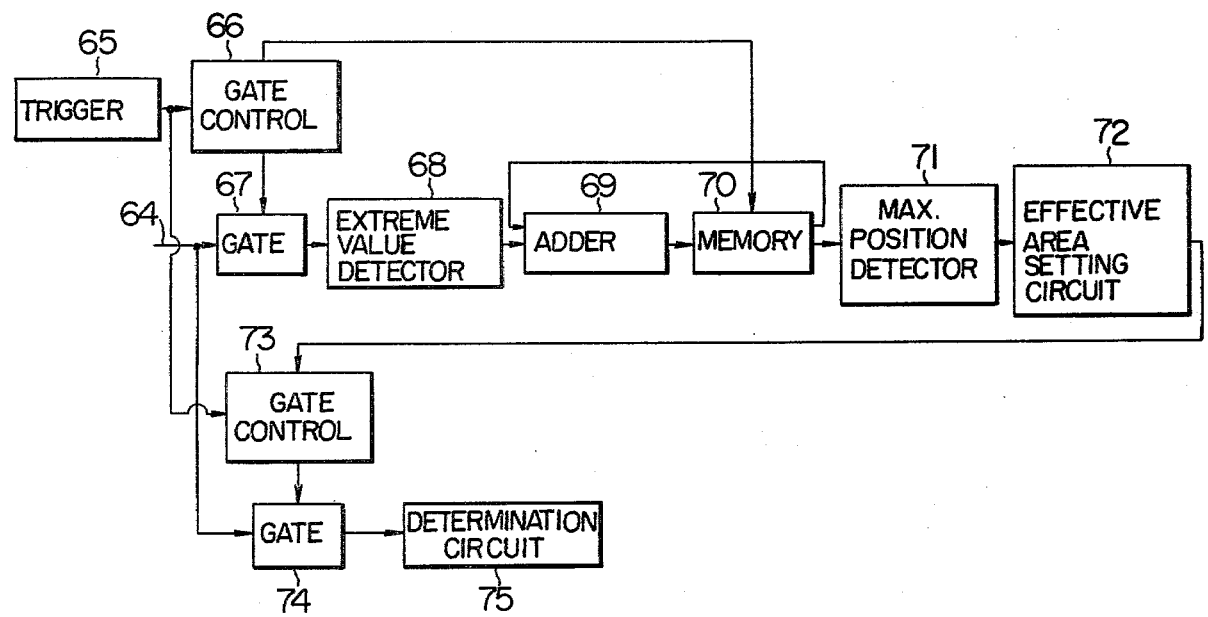
FIG. 11 shows a schematic configuration illustrating a processing circuit for an image signal obtained from the apparatus shown in FIG. 2.
Figure 13:
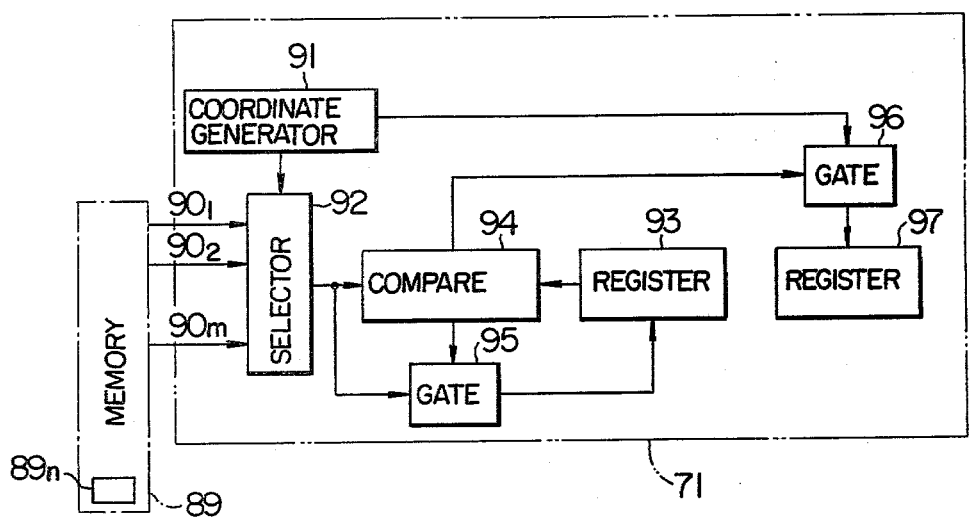
FIG. 13 is a circuit diagram showing a maximum value position detecting circuit shown in FIG. 11.
Figure 12:
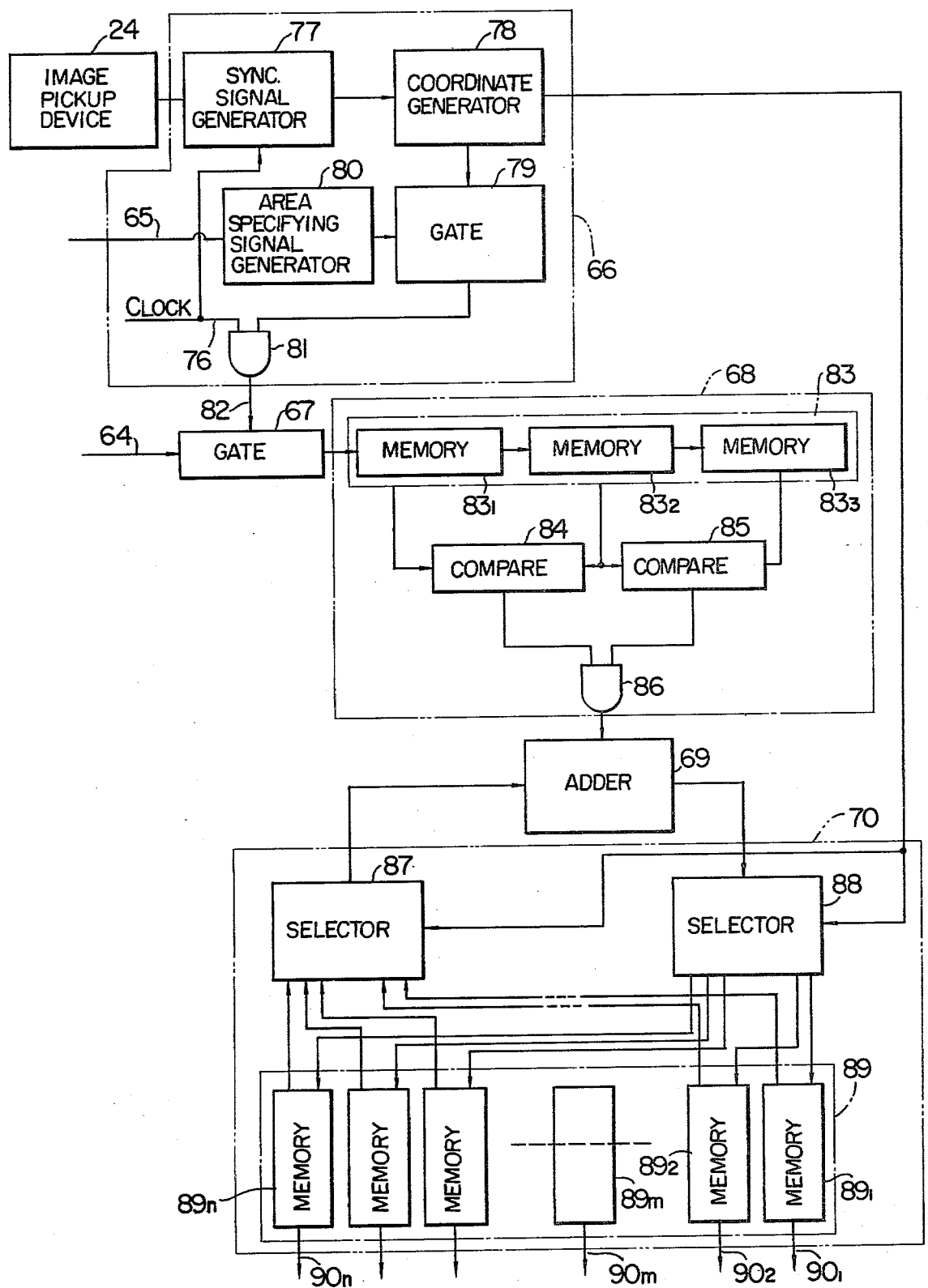
FIG. 12 is a circuit diagram showing a gate control circuit, a gate, an extreme value detection circuit, an adding circuit and a one-sweep type multi-value memory.

As described above, when the defect of the cylindrical surfaces 5 of the cylindrical bodies 1 are to be detected by the image pickup device 24, the cylindrical bodies 1 are pushed in line from the loading tray 2, as shown in FIGS. 4 and 9, in closely contacted fashion. Thus, when the images of the cylindrical surfaces 5 of the cylindrical bodies 1 are picked up by the image pickup device 24 while rotating the cylindrical bodies 1 and the resulting image signal is discriminated, a discriminated pattern as shown in FIG. 10 is obtained. This pattern includes dark areas at the positions of defects 61 which exist on the cylindrical surface 5 of the cylindrical body 1 and at boundaries 62 and 62' between the closely contacted end surfaces. If this pattern is tested, the boundaries 62 and 62' would also be determined as defect. Furthermore, since there exist a number of defects near the boundaries 62 and 62', if the image signal is discriminated by a white area and a black area and longitudinal distribution of frequency thereof is simply determined, the distribution of frequency would be flat or a gentle slope so that actual boundaries could not be determined because peak frequency would extend over a wide range. As described above, the image pickup device 24 of the detecting head 6 produces the pattern as shown in FIG. 10, as the image signal 64. As shown in FIG. 11, this image signal 64 is processed by a gate control circuit 66 which is operated by a trigger signal 65 which is a horizontal synchronization signal, (hereinafter abbreviated as "synch." signal) a gate 67 which gates or degates the image signal 64 by a gate signal produced from the gate control circuit 66, a peak detection circuit 68, an adding circuit 69, a one-sweep multi-value memory 70, a maximum value position detecting circuit 71, an effective test area setting circuit 72, a gate control circuit 73 which is operated by the output signal of the effective test area setting circuit 72 and the trigger signal 65, a gate 74 which gates or degates the image signal 64 by a gate signal produced from the gate control circuit 73 and a determination circuit 75 which determines any defect on an outer surface of the cylindrical body 1 by the image signal produced from the gate 74. In this manner, the outer surface of the cylindrical body 1 is tested for any defect of a predetermined size and a predetermined shape. As shown in FIG. 12, the gate control circuit 66 comprises a synch. signal generating circuit 77 which generates a scan synch. signal for the image pickup device 24 in response to a basic clock signal 76, a coordinate generating circuit 78 which generates a coordinate on an image plane in response to the synch. signal from the synch. signal generating circuit 77, an area specifying signal generating circuit 80 which generates a signal for specifying an area of extreme value detection in response to the synch. signal, a gate circuit 79 for producing a gate signal from the outputs of the coordinate generating circuit 78 and the area specifying signal generating circuit 80, and a gate circuit 81 which gates the output of the gate circuit 79 by the clock signal 76 to produce a sampling pulse 82 for the specified area only. Gate circuit 67 is composed of an A/D converter which samples the image signal 64 by the sampling pulse 82 for A/D conversion. The extreme value detection circuit 68 comprises a shift register 83 which receives and stores the video signals of three successive picture elements at memory elements $83_3$, $83_2$ and $83_1$ in time sequence, a compare circuit which produces an output when the content of the memory element $83_2$ is larger than the content of the memory element $83_1$, a compare circuit 85 which produces an output when the content of the memory element $83_2$ is smaller than the content of the memory element $83_3$, and a logical gate 86 which determines a valley when both the compare circuit 84 and the compare circuit 85 produce the outputs incidentally. An adding circuit 69 is activated for adding operation by the output signal from the extreme value detection circuit 68. A one-sweep multi-value memory 70 comprises a memory 89 which has addresses $89_1$, $89_2$, ... $89_m$, ... $89_n$ each allotted to each picture element and stores the frequency of the occurrence of a valley in the area specified by the area specifying signal generated by the area specifying signal generating circuit 80, a selection circuit 87 which causes the content of the address (coordinate) corresponding to the picture element which is currently being applied in the memory element $83_2$ from the output of the coordinate generating circuit 78 to be applied to the adding circuit 69, and a selection circuit 88 which causes the sum frequency of the adding circuit 69 to be stored at the address corresponding to the picture element which is currently being applied to the memory element $83_2$. As shown in FIG. 13, a maximum value position detecting circuit 71 is shown for only one maximum value position detection and m is smaller than n. The maximum value detection circuit 71 comprises a coordinate generating circuit 91 which sequentially generates picture element coordinates corresponding to the addresses $89_1$–$89_m$ of the memory 89, a selection circuit 92 which causes the content of the memory 69 to be read out from the address corresponding to the coordinate value provided from the coordinate generating circuit 91, a register 93 which stores a maximum value of the contents at the addresses $89_1$–$89_m$, a compare circuit 94 which compares the content of the register 93 with the content of the memory element selected by the selection circuit 92 and produces an output when the latter is larger than the former, a gate circuit 95 which causes the content selected by the selection circuit 92 to be stored in the register 93 when the compare circuit 94 produces the output, a gate circuit 96 which causes the coordinate signal produced from the coordinate generating circuit 91 to be read when the compare circuit 94 produces the output, and a coordinate register 97 which updates the coordinate when the gate circuit 96 produces an output.

The memory 89 of the one-sweep multi-value memory 70 is initially cleared to zero.

Figure 14A:
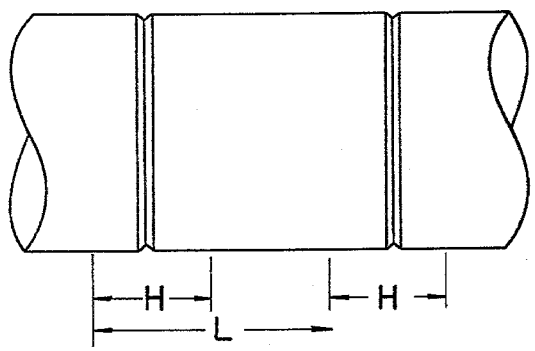
FIG. 14a shows a cylindrical body.
Figure 14B:
FIG. 14b shows a waveform of an image signal derived from an image pickup device.
Figure 14C:
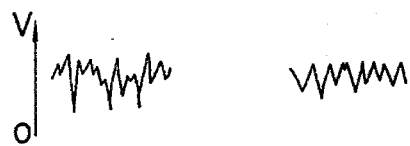
FIG. 14c shows a waveform of an image signal from a specified area.
Figure 14D:
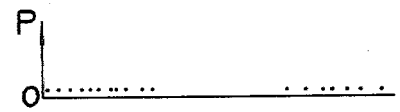
FIG. 14d shows plots of valley points of an image signal derived from a raster component.

Then, the image pickup device 24 of the detecting head 6 is electrically scanned by the synch. signal from the synch. signal generating circuit 77, and it detects one sweep of the image signal 64, as shown in FIG. 14b. The area specifying signal generating circuit 80 produces a "1" area specifying signal for section O−H and section L−L+H in response to the horizontal synch. signal (trigger signal) 65 generated at left end in FIG. 14a. In response to the area specifying signal, the A/D converter of the gate 67 is activated so that the image signal is sampled only for the above sections, as shown in FIG. 14c. At the same time, it is sampled by the clock pulse signal 76 and converted to digital signal. The digitalized image signal is then applied to the shift register 82 of the extreme value detection circuit 68 and stored in the memory elements $88_1$, $88_2$ and $88_3$ of the shift register 83. The three-picture element image signals stored successively in the memory elements $88_1$, $88_2$ and $88_3$ are compared in the compare circuit 85 to determine whether the content of $83_2$ is smaller than the content of $83_3$. If the content of $83_2$ is smaller than the content of $83_1$ and the content of $83_2$ is smaller than the content of $83_3$, it is determined that the content of $83_2$ is a minimum value and the logical gate circuit 86 produces an output indicating a minimum value position. Thus, the extreme value detecting circuit 88 detects the minimum value position of the image signal and supplies that information to the adder 69 so that the adder 69 adds "1" to that address of the memory 89 of the one-sweep multi-value memory 70 which corresponds to the minimum value position. FIG. 14d shows plots of the minimum value positions detected from the image signal shown in FIG. 14c. On the other hand, since the cylindrical body 1 is rotated by the rotating rollers 18 and 18', when the image pickup device 24 is activated by the sequential horizontal synch. signal (trigger signal), a number of rasters are scanned at different positions so that a number of image signals 64 are detected. The minimum value position of the image signals 64 is detected by the extreme value detecting circuit 68 and added to the respective addresses of the memory 89.

The adding circuit 69 sequentially adds to the frequency data stored at the address of memory 89 selected by the selection circuit 87 and writes the updated frequency data to the address of the same memory selected by the selection circuit 88. The above process is repeated for a number of rasters so that the memory 89 stores a distribution of frequency of the occurrence of the extreme values for the respective picture elements. In a normal surface such as machined surface, e.g. grinded surface, or sintered surface, the image signal thereof is representative of the roughness of the surface and the minimum value position of the image signal changes at random.

Figure 14E:
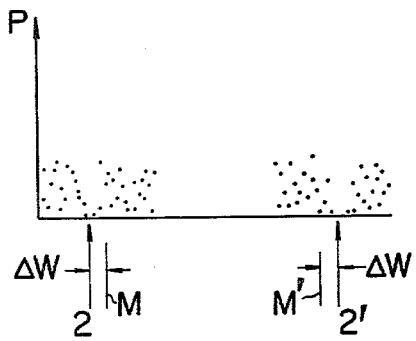
FIG. 14e shows distribution of frequency of the valley points of the image signal.

However, the boundaries 62 and 62' defined by the end surfaces of the cylindrical bodies 1 always exhibit the minimum value. Therefore, the distribution of the frequency of the minimum value positions is uniformly at a low level for the normal surface while it sharply rises at the boundaries 62 and 62', as shown in FIG. 10. Namely, at positions slightly away from the boundaries 62 and 62', the distribution of the frequency is at low level. Accordingly, by determining the address or coordinate at which the content of the memory 89 assumes the maximum value within each range corresponding to the section H, by the maximum value position detecting circuit 71, the position (or coordinate) of the boundary can be determined. The compare circuit 94 compares the content of the register 93 with the content of the address of the memory 89 selected by the selection circuit 92 and produces an output when the latter content is larger than the former content. This output activates the gate circuits 95 and 96 which cause the content read out by the selection circuit 92 to be transferred to the register 93 and causes the picture element coordinate produced from the coordinate generating circuit 91 to be transferred to the coordinate register 97. When the memory 89 has been scanned in this manner, the register 93 stores the maximum value of the content of the memory 89 while the coordinate register 97 stores the corresponding picture element coordinate. Accordingly, the last picture element coordinate stored in the coordinate register 97 is the picture element coordinate of the boundaries 62 and 62' of the cylindrical bodies 1. By adding thereto or subtracting therefrom a small value ΔW which has been preset by the effective test area setting circuit 72, a wide effective test area having masking ends defined by inner postiions M and M' as shown in FIG. 14e is established. By driving the gate control circuit 73 and activating the gate 74 in accordance with the instruction of the established effective test area, the image signal can be completely eliminated for the section ΔW measured from the boundaries of the cylindrical bodies 1.

As disclosed in the embodiment of the copending U.S. Application entitled "Surface Defect Inspection Apparatus" previously mentioned, the image signal is processed in the processing circuit 75 such that an average level $\overline{V}'$ of the image signal derived from the image pickup device 24 during the first revolution of the cylindrical body 1 is determined and stored, and the image signal derived from the image pickup device 24 during the second revolution is discriminated by a threshold $V_a' = k_a'\overline{V}'$ (where $k_a' > 1$) which is higher than the average level $\overline{V}'$ and a threshold $V_b = k_b'\overline{V}'$ (where $k_b' > 1$) which is lower than the average level $\overline{V}'$, and if it is higher than the higher threshold, it is determined as a broken cavity, and if it is lower than the lower threshold, it is determined as a pit or crack or a deeply broken cavity continuous to the broken cavity. The pit and the crack are further classified by determining if the relation $L^2 - 4\pi S > \epsilon$ is met, where L is the length of contour and S is the area thereof. The area of each classified defect pattern is calculated to determine whether it exceeds a maximum allowable limit. Total area of the respective classified defect patterns is also calculated to determine if it exceeds a maximum allowable limit. In this manner, each of the cylindrical bodies are graded.

Figure 15:
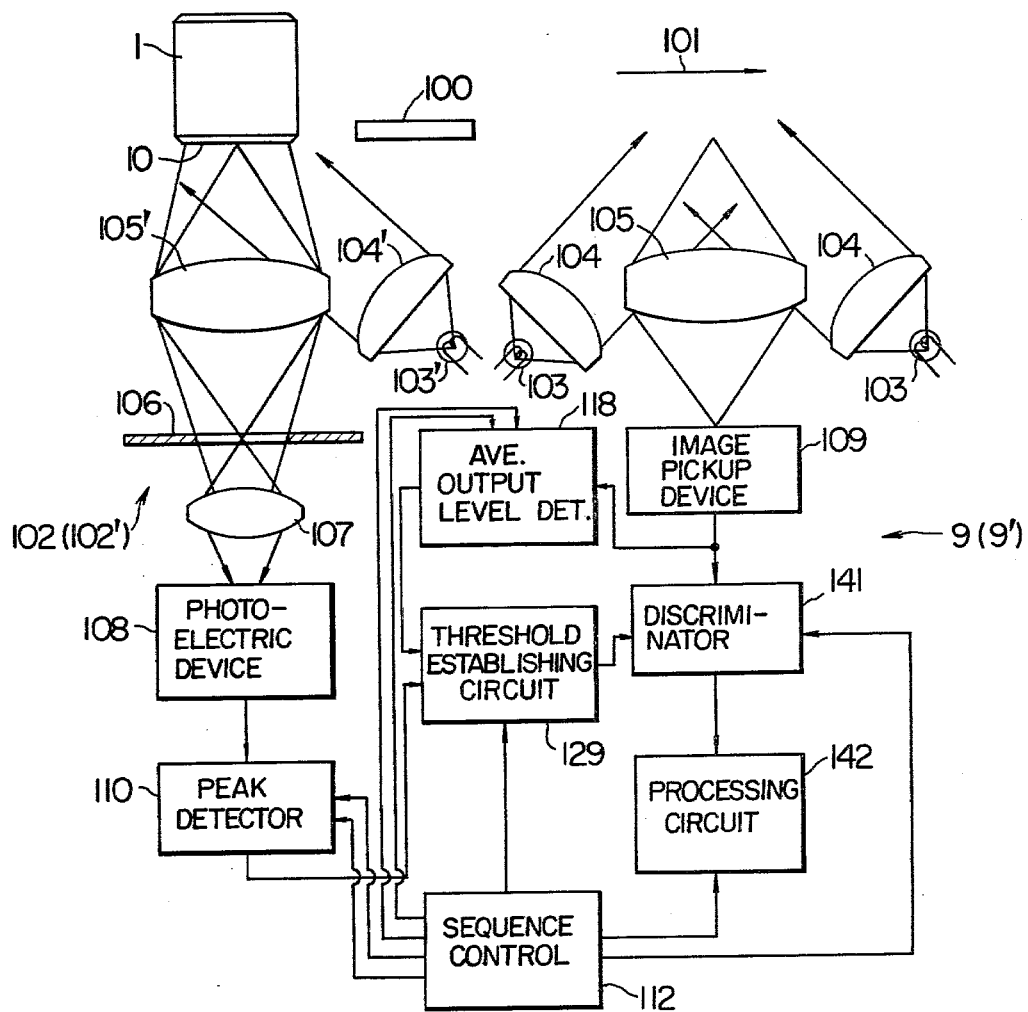
FIG. 15 shows a schematic configuration illustrating an auxiliary detecting head, a main detecting head and a major circuit shown in FIG. 8.

A method for determining a threshold when the image signal derived from the detecting heads 9 and 9' by picking up the image of the opposite end surfaces 10 of the cylindrical body 1 is discriminated by the predetermined threshold $V_c$ to produce a discriminated pattern for processing, is explained in detail. As for the cylindrical surface, since it is detected by the image pickup device while the cylindrical body is rotated at the same position, the average level corresponding to an average brightness may be obtained during the first revolution of the cylindrical body and the defect of the cylindrical surface may be determined during the second revolution as shown in FIG. 11. As for the end surfaces, however, since the defect is determined while the cylindrical body 1 is transported in one direction by the conveyer 47, the threshold is adjusted in the following manner. The cylindrical body 1 is mounted in the left channel 48 in each block of the conveyer 47 and a member 100 having a reference surface is attached to the right side of each block of the conveyer 47 with the reference surface being substantially aligned with the end surface 10 of the cylindrical body 1. The conveyer 47 which acts as a transporting unit is continuously moved in the direction of an arrow 101 at a high speed. As shown in FIG. 15, along the path of the conveyer which continuously transports the cylindrical body 1 and the member 100, auxiliary detecting heads 102 and 102' are arranged on the left side and the main detecting heads 9 and 9' are arranged on the right side. The auxiliary detecting heads 102 and 102' each comprises a lamp 103', a projecting lens 104', a focusing lens 105', a stationary mask 106, a condenser lens 107 and a photoelectric element 108. The photoelectric element 108 may be a photomultiplier, photo-diode, photo-transistor, photocell or the like.

Figure 16:
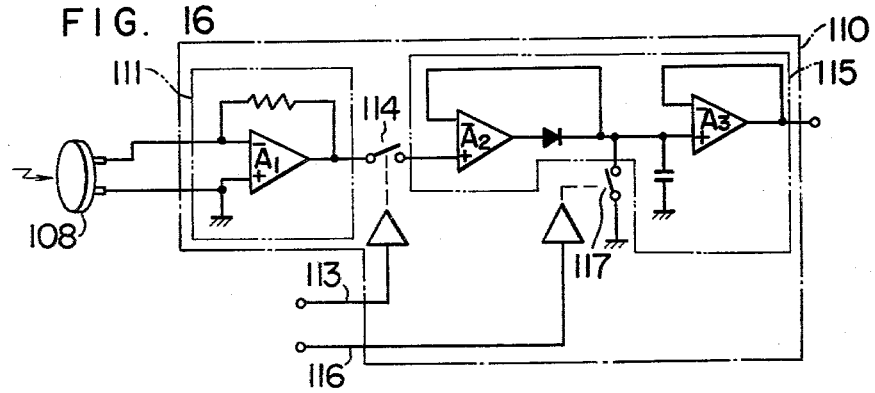
FIG. 16 shows a circuit diagram of a peak detector shown in FIG. 15.
Figure 19:
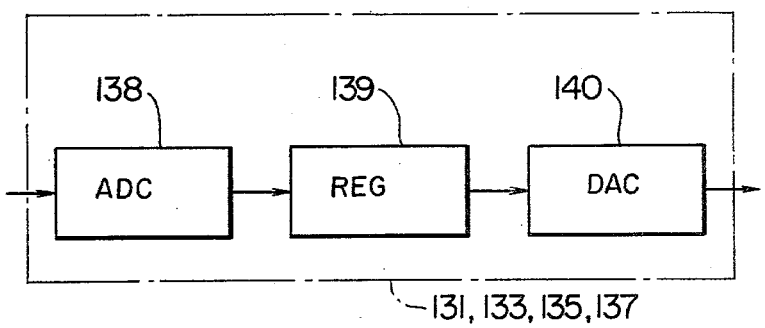
FIG. 19 shows a circuit diagram of a holding circuit shown in FIG. 18.

The main detecting head 9 comprises a lamp 103 to allow the inspection of the surface of the cylindrical body 1 or the recognition of pattern, projecting lenses 104 for projecting collimated lights from opposite oblique directions, a focusing lens 105 and an image pickup device 109 such as linear image sensor or charge coupled device. Numeral 110 denotes a peak detector which senses condensed light reflected from the entire area of the end surface 10 of the cylindrical body 1 or the reference surface of the member 100, that is, the light at optically averaged level, by the photoelectric element 108 and detects the maximum value of the output of the photoelectric element 108. In particular, the peak detector 110 is constructed as shown in FIG. 16. It comprises an amplifier circuit 111 which amplifies the signal derived from the photoelectric element 108, a switch 114 which is connected to the amplifier circuit 111 and actuated by a gate signal 113 produced from a sequence control circuit 112, a peak holding circuit which holds a peak of the signal derived from the amplifier circuit 111 through the switch 114, and a switch 117 which is actuated by a hold reset signal 116 from the sequence control circuit 112 to cancel the voltage held in a capacitor C of the peak holding circuit 115. Numeral 118 denotes an average output level detector which is scanned as shown by an arrow 27 in FIG. 3 by transporting the member 100 by the conveyer 47 at a constant speed. It may be electrically scanned in the direction of an arrow 28 by an image pickup element 109 such as an image sensor to produce an average output level of the image signal of the reference surface of the member 100 picked up by the main detecting head 9 or 9'. More particularly, the average output level detector 118 is constructed as shown in FIG. 17. It comprises a switch 120 which is connected to the image pickup element 109 and actuated by a gate signal 119 produced by the sequence control circuit 112, an integration circuit 121 which is connected to the switch 120 and integrates the image signal derived from the image pickup element 109, a switch 123 which is connected to a D.C. power supply 122 and actuated by the gate signal 119, an integration circuit 124 which is connected to the switch 123 and integrates a constant voltage signal derived from the D.C. power supply 122, switches 126 and 127 which are actuated by a reset signal 125 from the sequence control circuit 112 to cancel the voltage charged in capacitors of the integration circuits 121 and 124, and a divider 128 which divides the voltage $V_s$ produced by the integration circuit 121 by the voltage $V_t$ produced by the integration circuit 124 to produce an average output level signal $V_3$. Numeral 129 denotes a threshold establishing circuit which determines a threshold $V_c$ by carrying out the operation of $V_c = k \cdot V_2 \cdot (V_3/V_1)$, where k is a coefficient, $V_1$ is the maximum value detected by the peak detector 110 for the reference surface of the member 100, $V_2$ is the maximum value detected by the peak detector 100 for the end surface 10 of the cylindrical body 1 and $V_3$ is the average output level detected by the average output level detector 118 for the reference surface of the member 100. More particularly, the threshold establishing circuit 129 is constructed as shown in FIGS. 18 and 19. It comprises a switch 130 which is actuated by a command from the sequence control circuit 112, a hold circuit 131 which holds the maximum value $V_1$ produced by the peak detector 110, a divider 132 which divides the maximum value $V_2$ produced by the peak detector 110 by the maximum value $V_1$ produced by the hold circuit 131, a hold circuit 133 which holds the output $V_2/V_1$ of the divider 132, a hold circuit 137 which holds an average value of the output produced by the average output level detector 118, a multiplier 134 which multiplies the average output level $V_3$ produced by the hold circuit 137 by the output $V_2/V_1$ produced by the hold circuit 133, a hold circuit 135 which holds the product $V_3 \cdot (V_3/V_1)$ of the multiplier 134, an amplifier 136 which multiplies the output of the hold circuit 135 with a coefficient $k_a$ which is larger than unity, and an amplifier 137 which multiplies the output of the hold circuit 135 with a coefficient $k_b$ which is smaller than unity. As shown in FIG. 19, the hold circuits 131, 133, 135 and 137 each comprises an A/D converter 138, a register 139 and a D/A converter 140. Numeral 141 (FIG. 15) denotes a discriminator circuit, which, as shown in FIG. 3, discriminates the image signal derived from the image pickup element (linear image sensor) 109 by scanning the end surface 10 of the cylindrical body 1 by utilizing the thresholds $V_a$ and $V_b$, which are higher and lower, respectively, than the average level derived from the threshold establishing circuit 129. Numeral 142 denotes a processing circuit which determines the defect condition of the end surface 10 of the cylindrical body 1 based on the discriminated signal derived from the discriminator circuit 141.

Figure 20:
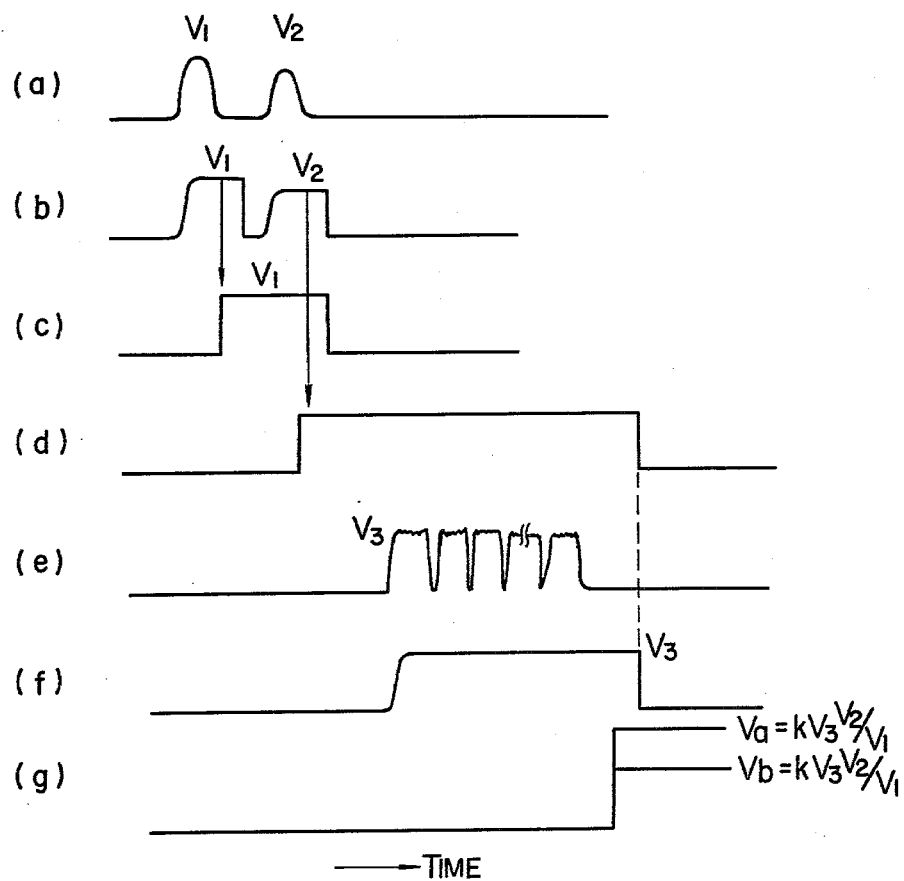
FIG. 20 shows signal waveforms derived from the circuits shown in FIGS. 16–18.

The reference surface of the member 100 and the end surface 10 of the cylindrical body 1 move with the conveyer 47 past the focusing planes of the auxiliary detecting head and the main detecting head in the direction of arrow 101. The auxiliary detecting head 102 or 102' senses the reflected light and focuses a real image thereof on the plane of the stationary mask 106. The stationary mask 106 has a circular transparent portion which is the same size as or slightly smaller than that of the real image of the end surface of the cylindrical body 1, and an opaque area surrounding the transparent area. The size of the reference surface of the member 100 should be selected such that the size of the real image thereof is slightly larger than the size of the transparent area of the mask. The light transmitted through the transparent area of the stationary mask 106 is collected by the condenser lens 107 onto the photoelectric element 108 which is comprised of photomultiplier, photodiode, photo-transistor, photo-cell or the like and which does not require high precision because an average brightness need only be obtained. Since the lights transmitted through the transparent area of the mask 106 are all collected onto the photoelectric element 108, they have been optically converted to an average level. The change in time of the output of the auxiliary detecting head is shown in FIG. 20(a). When the reference surface of the member 100 moves past the detecting head 102 or 102', a peak is produced. This peak $V_1$ is detected and held in the peak holding circuit 115 of the peak detector 110 as shown in FIG. 20(b). It is then read out and held in the hold circuit 131 of the threshold establishing circuit 129 as shown in FIG. 20(c). Subsequently, the end surface 10 of the cylindrical body 1 moves past the auxiliary detecting head and the maximum value $V_2$ is detected and held in the peak holding circuit 115 of the peak detector 110 as shown in FIG. 20(b). It is then read out and divided by the maximum value $V_1$ held in the holding circuit 131, in the divider 132 of the threshold establishing circuit 129. Thus, the holding circuit 133 now holds the value $V_2/V_1$ as shown in FIG. 20(d).

Subsequently, the reference surface of the member 100 moves past the focusing plane of the main detecting head 9 or 9', and is scanned at a constant speed in the direction of the arrow 27 in FIG. 3 as the member 100 is transported by the conveyer 47. Also it is electrically scanned in the direction of the arrow 28. As a result, the image pickup device 109 produces the image signal as shown in FIG. 20(e). This image signal is integrated by the integration circuit 121 of the average level detector 118, the output of which is divided by the divider 128 by the value $V_t$ which is proportional to the time to produce the average output level $V_3$ of the reference surface of the member 100. This average output level $V_3$ is held in the hold circuit 137 of the threshold establishing circuit 129 as shown in FIG. 20(f), and the output of which is multiplied by the value $V_2/V_1$ held in the holding circuit 133 in the multiplier circuit 134 to produce $\overline{V} = V_2 \cdot (V_3/V_1)$, which value is held in the holding circuit 135, the output of which is multiplied by the coefficients $k_a$ and $k_b$ to produce the thresholds $V_a = k_a \overline{V}$ and $V_b = k_b \overline{V}$, as shown in FIG. 20(g). Subsequently, the end surface of the cylindrical body 1 moves past the focal plane of the main detecting head, and it is scanned at a constant speed in the direction of the arrow 27 in FIG. 3 as the cylindrical body 1 is transported by the conveyer 42, and also electrically scanned in the direction of the arrow 28. As a result, the image pickup device 109 produces the image signal, which is discriminated in the discriminator circuit 141 by the thresholds $V_a$ and $V_b$ which are higher and lower, respectively, than the average level. The resulting discriminated pattern is fed to the processing circuit 142, which in turn examines the discriminated pattern to determine any defect on the end surface 10 of the cylindrical body 1.

The operation of the processing circuit 142 is disclosed in the copending U.S. Application, previously mentioned. Briefly, when the image signal level exceeds the higher threshold $V_a$, it is determined as the broken cavity, and when the image signal level does not exceed the lower threshold $V_b$, it is determined as the pit, crack or deeply broken cavity continuous to the broken cavity. Furthermore, if the relation $L^2 - 4\pi S < \epsilon$, where L is the length of the contour of the pattern, S is the area and $\epsilon$ is an arbitrary constant, is met, it is determined as the pit, and if the relation $L^2 - 4\pi S \geq \epsilon$ is met, it is determined as the crack. In this manner, the defect pattern on the end surface is classified to one of the broken cavity, pit and crack. The area of each classified pattern is examined to determine whether it is below the maximum allowable limit, and the total area of all of the classified patterns is examined to determine if it is below the maximum allowable limit. In this manner, the defect patterns are graded.

As described hereinabove, according to the present invention, a small defect (broken cavity, pit or crack) in the order of 50 $\mu$m which may exist on the cylindrical surface and the opposite end surfaces of the cylindrical body having the diameter of the order of 10 mm and the length of the order of 10 mm can be precisely detected automatically. Furthermore, according to the present invention, the cylindrical surfaces of cylindrical bodies can be tested up to the areas very close to the end surfaces (boundaries) while the cylindrical bodies are closely contacted to each other. Therefore, any defect which exist at the corner can be detected. Moreover, according to the present invention, the threshold by which the image signal is derived from the image pickup device can be automatically adjusted to compensate for the variance of the reflection factor of the cylindrical body and the aging of the illumination means. Accordingly, high precision defect inspection can be attained.

We claim:

1. A cylindrical body appearance inspection apparatus comprising:
   a cylindrical surface appearance detecting device including rotating means for rotating a cylindrical body to be inspected around an axis thereof at a constant speed, and detecting means for optically detecting reflected light indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface to thereby produce an image signal for each sampling;
   an end surface appearance detecting device including first transporting means for transporting a plurality of cylindrical bodies sequentially with axes thereof being arranged in parallel to each other, detecting means arranged to face the opposite end surfaces of the cylindrical body transported by said first transporting means for optically detecting reflected light indicative of a surface condition of small width band areas on the opposite end surfaces extending in the direction transverse to the direction of transport of the cylindrical bodies and for repeating the sampling detection of the opposite end surfaces as the cylindrical body is transported to scan the entire area of each of the opposite end surfaces to thereby produce an image signal for each sampling;

second transporting means for transporting the cylindrical body between said cylindrical surface appearance detecting device and said end surface appearance detecting device from one to the other; and test means for determining pass or fail or grade of any defect pattern which exists on the surface of the cylindrical body based on said image signals derived from said cylindrical surface appearance detecting device and said end surface appearance detecting device;

whereby the appearance of the cylindrical surface and the opposite end surfaces of the cylindrical body is automatically and optically inspected and wherein said detecting means of said end surface appearance detecting means includes an optical system for projecting collimated light beams onto the opposite end surfaces from opposite directions which are oblique and a solid-state image pickup device having photosensing elements arranged in at least one line with their photosensing surfaces arranged in parallel to the end surfaces to sense light rays reflected from the end surfaces of the cylindrical body in the direction transverse to the direction of transportation of the cylindrical body by said first transporting means.

2. A cylindrical body appearance inspection apparatus comprising:

a cylindrical surface appearance detecting device including rotating means for rotating a cylindrical body to be inspected around an axis thereof at a constant speed, detecting means for optically detecting reflected light indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface and to thereby produce an image signal for each sampling;

and end surface appearance detecting device including first transporting means for transporting a plurality of cylindrical bodies sequentially with axes thereof being arranged in parallel to each other, detecting means arranged to face the opposite end surfaces of the cylindrical body transported by said first transporting means for optically detecting reflected light indicative of a surface condition of small width band areas on the opposite end surfaces extending in the direction transverse to the direction of transport of the cylindrical bodies and for repeating the sampling detection of the opposite end surfaces as the cylindrical body is transported to scan the entire area of each of the opposite end surfaces to thereby produce an image signal for each sampling;

second transporting means for transporting the cylindrical body between said cylindrical surface appearance detecting device and said end surface appearance detecting device from one to the other; and test means for determining pass or fail or grade of any defect pattern which exists on the surface of the cylindrical body based on said image signals derived from said cylindrical surface appearance detecting device and said end surface appearance detecting device whereby the appearance of the cylindrical surface and the opposite end surfaces of the cylindrical body is automatically and optically inspected and wherein said detecting means of said cylindrical surface appearance detecting device includes an optical system for projecting collimated light beams onto the cylindrical surface from opposite directions which are oblique to the axial direction and a solid-state image pickup device having photosensing elements arranged in at least one line with their photosensing surfaces arranged in parallel to the cylindrical surface to sense base line light rays parallel to the axial line of the cylindrical body, of the light reflected by the cylindrical surface, and said detecting means of said end surface appearance detecting device includes an optical system for projecting collimated lights onto the opposite end surfaces from opposite oblique directions and a solid-state image pickup device having photosensing elements arranged in at least one line with their photosensing surfaces being arranged in parallel to the end surfaces to sense light rays reflected from the end surfaces of the cylindrical body in the direction transverse to the direction of transportation of the cylindrical body by said first transporting means.

3. A cylindrical body appearance inspection apparatus comprising:

a cylindrical surface appearance detecting device including rotating means for rotating a plurality of cylindrical bodies around their axes at a constant speed with the cylindrical bodies being closely contacted side by side, detecting means for optically detecting cylindrical surfaces of the cylindrical bodies being rotated by said rotating means and one-dimensionally scanning an image thereof on a plane of real image to produce an image signal of an axial base line on the cylindrical surface of the cylindrical body, and effective area setting means for quantizing said image signal derived from said detecting means to picture element signals, comparing one picture element signal with adjacent picture element signal to determine an extreme value coordinate, adding the extreme value coordinate of each scan together to develop distribution of frequency, and setting an effective area of the image signal derived from said detecting means based on boundary coordinate representing a maximum value or a minimum value of the distribution of frequency;

an end surface appearance detecting device including first transporting means for sequentially transporting said cylindrical bodies with the axes of the cylindrical bodies being arranged in parallel to each other and detecting means for optically detecting opposite end surfaces of each cylindrical body being transported by said first transporting means and two-dimensionally scanning images thereof on a plane of real image to produce an image signal;

second transporting means for transporting the cylindrical bodies between said cylindrical surface appearance detecting device and said end surface appearance detecting device from one to the other; and test means for determining pass or fail or grade of any defect pattern which exists on the surface of the cylindrical body based on the image signal derived from said end surface detecting device and the effective area of the image signal determined by said effective area setting means of said cylindrical surface appearance detecting device;

whereby the appearance of the cylindrical surface and the opposite end surfaces of the cylindrical body is optically and automatically inspected.

4. A cylindrical body appearance inspection apparatus according to claim 3, wherein a pair of said detecting means of said end surface appearance detecting device are arranged on both sides of the transport path of said first transporting means in facing relation to the opposite end surfaces of the cylindrical body.

5. A cylindrical body appearance inspection apparatus comprising:

a cylindrical surface appearance detecting device including rotating means for rotating a cylindrical body around an axis thereof at a constant speed, detecting means for optically detecting a cylindrical surface of the cylindrical body being rotated by said rotating means, and one-dimensionally scanning an image thereof on a plane of real image to produce an image signal of an axial base line on the cylindrical surface of the cylindrical body, and a threshold establishing means for establishing a threshold $V'=k'\overline{V'}$, where k' is a coefficient, based on an average level $\overline{V'}$ of the image signal produced by said detecting means during the first revolution of said cylindrical body;

an end surface appearance detecting device including first transporting means for sequentially transporting a plurality of said cylindrical bodies with their axes being arranged in parallel to each other and having a member attached thereto between one cylindrical body receiving position and adjacent cylindrical body receiving position, said member having a reference surface which is used as a brightness reference, auxiliary detecting means arranged ahead of transport path to pick up images of the reference surface of said member and the opposite ends of the cylindrical body to produce brightness level signals $V_1$ and $V_2$ of the images, detecting means for optically detecting the reference surface of said member and the opposite end surfaces of the cylindrical body and two-dimensionally scanning the images on planes of real image to produce image signals, and threshold establishing means for establishing a threshold $V=kV_2\cdot(V_3/V_1)$, where k is a coefficient, based on an average output level $V_3$ of the image signal derived by said detecting means for the reference surface of said member and the average brightness levels $V_1$ and $V_2$ derived from said auxiliary detecting means;

second transporting means for transporting the cylindrical body between said cylindrical surface appearance detecting device and said end surface appearance detecting device from one to the other; and test means for discriminating the image signal derived from said detecting means of said cylindrical surface appearance detecting device by the threshold V', discriminating the image signal derived from said detecting means of said end surface appearance detecting device by the threshold V and determining pass or fail or grade of any defect pattern which exists on the surface of the cylindrical body based on the two discriminated signals;

whereby the appearance of the cylindrical surface and the opposite end surfaces of the cylindrical body is optically and automatically inspected.

6. A cylindrical body appearance inspection apparatus comprising:

a cylindrical surface appearance detecting device including rotating means for rotating a cylindrical body to be inspected around an axis thereof at a constant speed, detecting means for detecting, by scanning, reflected light indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface to thereby produce a two dimensional scanning image signal;

an end surface apparatus detecting device including first transporting means for transporting a plurality of cylindrical bodies sequentially with axes thereof being arranged in parallel to each other, detecting means arranged to face the opposite end surfaces of the cylindrical body transported by said first transporting means for detecting, by scanning, reflected light indicative of a surface condition of small width band areas on the opposite end surfaces extending in the direction transverse to the direction of transport of the cylindrical bodies and for repeating the sampling detection of the opposite end surfaces as the cylindrical body is transported to scan the entire area of each of the opposite end surfaces to thereby produce a two dimensional scanning image signal second transporting means for transporting the cylindrical bodies between said cylindrical surface appearance detecting device and said end surface appearance detecting device from one to the other; and test means for determining pass or fail or grade of any defect pattern which exists on the surface of the cylindrical body based on the image signals derived from said cylindrical surface appearance detecting device and said end surface appearance detecting device whereby the appearance of the cylindrical surface and the opposite end surfaces of the cylindrical body is optically and automatically inspected.

7. A cylindrical body appearance inspection apparatus according to claim 6, wherein said detecting means of said cylindrical surface appearance detecting device includes an optical system for projecting collimated light beams obliquely onto the cylindrical surface from at least opposite directions, focusing lens means for focusing the reflected light from the cylindrical surface of the cylindrical body, and a solid-state image pickup device having photosensing elements arranged in at least one line parallel to the axis of said cylindrical body with the photosensing surfaces thereon being arranged in parallel to the cylindrical surface.

8. A cylindrical body appearance inspection apparatus comprising:
a cylindrical surface appearance detecting device including rotating means for rotating a cylindrical body to be inspected around an axis thereof at a constant speed, detecting means for detecting by scanning a reflected image indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface to thereby produce a two dimensional scanning image signal;
an end surface appearance detecting device including first transporting means for transporting a plurality of cylindrical bodies sequentially with axes thereof being arranged in parallel to each other, detecting means arranged to face the opposite end surfaces of the cylindrical body transported by said first transporting means and includes an optical system for projecting collimated light beams obliquely onto the opposite end surfaces from at least opposite directions, focusing lens means for focusing the reflected light from the opposite end surfaces of the cylindrical body, and a solid-state image pickup device having photosensing elements arranged in at least one line extending in a direction transverse to the direction of transport with the photosensing surface thereof being arranged in parallel to an end surface for detecting, by scanning, reflected light indicative of a surface condition of small width band areas on the opposite end surfaces extending in the direction transverse to the direction of transport of the cylindrical bodies and for repeating the sampling detection of the opposite end surfaces as the cylindrical bodies are transported to scan the entire area of each of the opposite end surfaces to thereby produce a two dimensional scanning image signal;
second transporting means for transporting the cylindrical bodies between said cylindrical surface appearance detecting device and said end surface appearance detecting device from one to the other; and
test means for determining pass or fail or grade of any defect pattern which exists on the surface of the cylindrical body based on said image signals derived from said cylindrical surface appearance detecting device and said end surface appearance detecting device
whereby the appearance of the cylindrical surface and the opposite end surfaces of the cylindrical body is automatically and optically inspected.

9. A cylindrical body appearance inspection apparatus according to claim 8, wherein said detecting means of said cylindrical surface appearance detecting device includes an optical system for projecting collimated light beams obliquely onto the cylindrical surface from at least opposite directions, focusing lens means for focusing the reflected light from the cylindrical surface of the cylindrical body, and a solid-state image pickup device having photosensing elements arranged in at least one line with their photo-sensing surface being arranged in parallel to the cylindrical surface.

10. A cylindrical body appearance inspection apparatus comprising:
a cylindrical surface appearance detecting device including rotating means for rotating a cylindrical body to be inspected around an axis thereof at a constant speed, detecting means for detecting, by scanning, reflected light indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface to thereby produce a two dimensional scanning image signal, and effective area setting means for setting the effective area of the image signal;
an end surface appearance detecting device including first transporting means comprising a rotating disc being rotated by rotating drive unit at a constant speed and arranged for receiving said cylindrical bodies and for transporting a plurality of cylindrical bodies sequentially with axes thereof being arranged in parallel to each other, detecting means arranged to face the opposite end surfaces of the cylindrical bodies transported by said first transporting means for detecting, by scanning, reflected light indicative of a surface condition of small width band areas on the opposite end surfaces extending in the direction transverse to the direction of transport of the cylindrical bodies, and for repeating the sampling detection of the opposite end surfaces as the cylindrical body is transported to scan the entire area of each of the opposite end surfaces to thereby produce a two dimensional scanning image signal;
second transporting means for transporting the cylindrical bodies between said cylindrical surface appearance detecting device and said end surface appearance detecting device from one to the other; and
test means for determining pass, fail, or grade of any defect pattern which exists on the surface of the cylindrical body based on the image signal derived from said end surface detecting device and the effective area of the image signal determined by said effective area setting means of said cylindrical surface appearance detecting device
whereby the appearance of the cylindrical surface and the opposite end surfaces of the cylindrical body is optically and automatically inspected.

11. A cylindrical body appearance inspection apparatus comprising:
a cylindrical surface appearance detecting device including rotating means for rotating a plurality of cylindrical bodies around the axes thereof at a constant speed with the cylindrical bodies being arranged in a row, detecting means for detecting, by scanning, reflected light indicative of a surface condition of a small width base line band area, which is parallel to the axis of said cylindrical body, of a cylindrical surface of said cylindrical body rotated by said rotating means and for repeating the sampling detection of the band area as the cylindrical body rotates to scan the entire surface of the cylindrical surface to thereby produce a two dimensional scanning image signal;

an end surface appearance detecting device including first transporting means for transporting a plurality of cylindrical bodies sequentially with the axes thereof being arranged in parallel to each other, detecting means arranged to face the opposite end surfaces of the cylindrical bodies transported by said first transporting means for detecting, by scanning, reflected light indicative of a surface condition of small width band areas on the opposite end surfaces extending in the direction transverse to the direction of transport of the cylindrical bodies and for repeating the sampling detection of the opposite end surfaces as the cylindrical body is transported to scan the entire area of each of the opposite end surfaces to thereby produce a two dimensional scanning image;

second transporting means for transporting the cylindrical bodies between said cylindrical surface appearance detecting device and said end surface appearance detecting device from one to the other; and test means for determining pass, fail, or grade of any defect pattern which exists on the surface of the cylindrical body based on the image signals derived from said cylindrical surface appearance detecting device and said end surface appearance detecting device whereby the appearance of the cylindrical surface and the opposite end surfaces of the cylindrical body is optically and automatically inspected.

12. A cylindrical body appearance inspection apparatus comprising:
 (a) a cylindrical surface appearance detecting device including;
  (i) rotating means for rotating a plurality of cylindrical bodies around the aces thereof with the cylindrical bodies being arranged in a row,
  (ii) detecting means having an optical system for projecting collimated light beams obliquely onto the cylindrical surface from at least opposite directions, a focusing lens for focusing the reflected light from the cylindrical surface of each cylindrical body, a solid-state image pickup device having photosensing elements arranged in at least one line in parallel to the axis of the cylindrical body with their photosensing surfaces thereof being arranged in parallel to the cylindrical surface for detecting, by scanning, reflected light indicative of a surface condition of small width band areas of the cylindrical surface of the cylindrical body in parallel to the axis thereof and for repeating the sampling detection of said band area as the cylindrical body rotates to scan the entire surface of the cylindrical body to thereby produce a two dimensional scanning image signal, and effective area setting means for setting the effective area of the image signal, and
  (iii) moving means for moving said detecting means in parallel to the row of the cylindrical bodies from one end to the other end thereof;
 (b) an end surface appearance detecting device including first transporting means for transporting a plurality of cylindrical bodies sequentially with plurality of cylindrical bodies sequentially with axes thereof being arranged in parallel to each other, detecting means arranged to face the opposite end surfaces of the cylindrical body transported by said first transporting means for detecting, by scanning, reflected light indicative of a surface condition of small width band areas on the opposite end surfaces extending in the direction transverse to the direction of transport of the cylindrical bodies and for repeating the sampling detection of the opposite end surfaces as the cylindrical body is transported to scan the entire area of each of the opposite end surfaces to thereby produce a two dimensional scanning image signa;
 (c) second transporting means for transporting the cylindrical bodies between said cylindrical surface appearance detecting device and said end surface appearance detecting device from one to the other; and
 (d) test means for determining pass, fail, or grade of any defect pattern which exists on the surface of the cylindrical body based on the image signal derived from said end surface detecting device and the effective area of the image signal determined by said effective area setting means of said cylindrical surface appearance detecting device
 (e) whereby the appearance of the cylindrical surface and the opposite end surfaces of the cylindrical body is optically and automatically inspected.

13. A cylindrical body appearance inspection apparatus according to claim 12, wherein said cylindrical surface appearance detecting device includes third transporting means for shifting a row of the cylindrical bodies to a loading position, a cylindrical surface detecting position and an unloading position by intermittently shifting at least three rotating means arranged in parallel and coupled with a station position changeover mechanism.

14. A cylindrical body appearance inspection apparatus comprising:
 a cylindrical surface appearance detecting device including rotating means for rotating a plurality of cylindrical bodies around the axes thereof at a constant speed with the cylindrical bodies arranged in a row, detecting means for detecting, by scanning, reflected light indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface to thereby produce a two dimensional scanning image signal, and effective area setting means for quantizing said image signal derived from said detecting means to picture element signals, for adding said picture element signals of each scan together to develop distribution of frequency, and for setting an effective area of the image signal derived from said detecting means based on a boundary coordinate representing a maximum value or a minimum value of the distribution of frequency;
 an end surface appearance detecting device including first transporting means for transporting a plurality of cylindrical bodies sequentially with the axes thereof arranged in parallel to each other, detecting means arranged to face the opposite end surfaces of the cylindrical bodies transported by said first transporting means for detecting, by scanning, reflected light indicative of a surface condition of samll width band areas on the opposite end surfaces extending in the direction transverse to the direction of transport of the cylindrical bodies and for repeating the sampling detection of the opposite end surfaces as the cylindrical body is transported to scan the entire area of each of the opposite end surface to thereby produce a two dimensional scanning image signal;

second transporting means for transporting the cylindrical bodies between said cylindrical surface appearance detecting device and said end surface appearance detecting device from one to the other; and test means for determining pass, fail, or grade of any defect pattern which exits on the surface of the cylindrical body based on the image signals derived from said end surface detecting device and from the effective area of the image signal determined by said effective area setting means of said cylindrical surface appearance detecting device whereby the appearance of the cylindrical surface and the opposite end surfaces of the cylindrical body is optically and automatically inspected.

15. A cylindrical body appearance inspection apparatus comprising:

a cylindrical surface appearance detecting device including rotating means for rotating a cylindrical body to be inspected around an axis thereof at a constant speed with a plurality of cylindrical bodies being arranged in a row, detecting means for detecting, by scanning, reflected light indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface to thereby produce a two dimensional scanning image, effective area setting means for quantizing said image signal derived from said detecting means to picture element signals, for comparing one picture element signal with an adjacent picture element signal to determine an extreme value coordinate, for adding the extreme value coordinate of each scan together to develop a distribution of frequency and for setting an effective area of the image signal derived from said detecting means based on a boundary coordinate representing a maximum value or a minimum value of the distribution of frequency;

an end surface appearance detecting device including first transporting means for sequentially transporting said cylindrical bodies with the axes of the cylindrical bodies being arranged in parallel to each other, detecting means for detecting, by scanning, reflected light indicative of a surface condition of small width band areas on the opposite end surfaces extending in the direction transverse to the direction of transport of the cylindrical bodies and for repeating the sampling detection of the opposite end surfaces as the cylindrical body is transported to scan the entire area of each of the opposite end surfaces to thereby produce a two dimensional scanning image signal;

second transporting means for transporting the cylindrical bodies between said cylindrical surface appearance detecting device and said end surface appearance detecting device from one to the other; and test means for determining pass, fail, or grade of any defect pattern which exists on the surface of the cylindrical body based on the image signal derived from said end surface detecting device and the effective area of the image signal determined by said effective area setting means of said cylindrical surface appearance detecting device whereby the appearance of the cylindrical surface and the opposite end surfaces of the cylindrical body is optically and automatically inspected.

16. A cylindrical body appearance inspection apparatus comprising:

a cylindrical surface appearance detecting device including rotating means for rotating a cylindrical body to be inspected around an axis thereof at a constant speed, detecting means for detecting, by scanning, reflected light indicative of a surface condition of a small width base line band area, which is parallel to the axis of said cylindrical body, of a cylindrical surface of said cylindrical body being rotated by said rotating means and for repeating the sampling detection of the band area as the cylindrical body rotates to scan the entire surface of the cylindrical surface to thereby produce a two dimensional scanning image signal, and a threshold establishing means for establishing a threshold $V' = k'\overline{V}$, where $k'$ is a coefficient, based on an average level $\overline{V}'$ of the image signal produced by said detecting means during the rotation of said cylindrical body;

an end surface appearance detecting device including first transporting means for transpo-ting a plurality of cylindrical bodies sequentially with the axes thereof arranged in parallel to each other, detecting means arranged to face the opposite end surfaces of the cylindrical bodies transported by said first transporting means for detecting, by scanning, reflected light indicative of a surface condition of small width band areas on the opposite end surfaces extending in the direction transverse to the direction of transport of the cylindrical bodies and for repeating the sampling detection of the opposite end surfaces as the cylindrical body is transported to scan the entire area of each of the opposite end surface to thereby produce a two dimansional scanning image signal;

second transporting means for transporting the cylindrical bodies between said cylindrical surface appearance detecting device and said end surface appearance detecting device from one to the other; and test means for discriminating the image signal derived from said detecting means of said cylindrical surface appearance detecting device by the threshold $V'$ and for determining pass, or fail, or grade of any defect pattern which exists on the surface of the cylindrical body based on the discriminated signal and the image signal derived from said end surface appearance detecting device whereby the appearance of the cylindrical surface and the opposite end surfaces of the cylindrical body is optically and automatically inspected.

17. A cylindrical body appearance inspection apparatus comprising:

a cylindrical surface appearance detecting device including rotating means for rotating a cylindrical body to be inspected around an axis thereof at a constant speed, detecting means for detecting, by scanning, reflected light indicative of a surface condition of a small width base line band area, which is parallel to the axis of said cylindrical body, of a cylindrical surface of said cylindrical body rotated by said rotating means and for repeating the sampling detection of the band area as the cylindrical body rotates to scan the entire surface of the cylindrical surface to thereby produce a two dimensional scanning image signal;

an end surface appearance detecting device including first transporting means for sequentially transporting a plurality of cylindrical bodies with the axes thereof being arranged in parallel to each other and having a member attached thereto between one cylindrical body receiving position and an adjacent cylindrical body receiving position, said member having a reference surface which is used as a brightness reference, auxiliary detecting means arranged ahead of the transport path to pick up images of the reference surface of said member and the opposite ends of the cylindrical body to produce average brightness level signals $V_1$ and $V_2$ of the images, detecting means for optically detecting the reference surface of said member and the opposite end surfaces of the cylindrical body and for two-deminsional scanning the reflected light to produce image signals, and threshold establishing means for establishing a threshold $V=kV_2\cdot(V_3/V_1)$, where k is a coiefficient, based on an average output level $V_3$ of the image signal derived by said detecting means for the reference surface of said member and the average brightness levels $V_1$ and $V_2$ derived from said auxiliary detecting means;

second transporting means for transporting said cylindrical bodies between said cylindrical surface appearance detecting device and said end surface appearance detecting device from one to the other; and test means for discriminating the image signal derived from said detecting means of said end surface appearance detecting device by the threshold V and for determining pass or fail or grade of any defect pattern which exists on the surface of the cylindrical body based on the discriminated signal and the image signal derived from said cylindrical surface appearance detecting device whereby the appearance of the cylindrical surface and the opposite end surfaces of the cylindrical body is opticaally and automatically inspected.

* * * * *